United States Patent
Ozbalik et al.

(10) Patent No.: US 7,208,452 B2
(45) Date of Patent: Apr. 24, 2007

(54) PROCESS FOR MANUFACTURING ALKYLPHOSPHONATE MONOESTERS

(75) Inventors: Nubar Ozbalik, Midlothian, VA (US); Roger M. Sheets, Glen Allen, VA (US)

(73) Assignee: Afton Chemical Intangibles, LLC, Richmond, VA (US)

( * ) Notice: Subject to any disclaimer, the term of this patent is extended or adjusted under 35 U.S.C. 154(b) by 383 days.

(21) Appl. No.: 10/439,751

(22) Filed: May 16, 2003

(65) Prior Publication Data

US 2004/0230068 A1 Nov. 18, 2004

(51) Int. Cl.
C10M 137/12 (2006.01)
C07F 9/02 (2006.01)

(52) U.S. Cl. .................................. 508/422; 558/117
(58) Field of Classification Search .......... 558/110; 508/422

See application file for complete search history.

(56) References Cited

U.S. PATENT DOCUMENTS

| | | | |
|---|---|---|---|
| 2,784,208 A | | 3/1957 | Ries et al. |
| 3,778,375 A | | 12/1973 | Braid et al. |
| 3,798,162 A | | 3/1974 | Dickert et al. |
| 3,927,232 A | | 12/1975 | Dickert et al. |
| 5,302,707 A | | 4/1994 | Campbell et al. |
| 5,359,115 A | | 10/1994 | Campbell et al. |
| 5,420,328 A | * | 5/1995 | Campbell ............... 558/110 |
| 5,910,469 A | * | 6/1999 | Carey et al. .......... 508/422 |

FOREIGN PATENT DOCUMENTS

| | | |
|---|---|---|
| CN | 85 1 00469 A | 1/1986 |
| DE | 1 807 924 | 6/1969 |
| DE | 2 551 598 | 4/1977 |
| GB | 1 247 541 | 9/1971 |
| GB | 1 559 883 | 1/1980 |

OTHER PUBLICATIONS

Horiuchi, Kiyoshi; Okamoto, Yoshiki; Sakurai, Hiroshi; "Synthesis and properties of Monoethyl n-alkylphosphonates," Kogyo Kagaku Zasshi; (1967), 70(7), 1261-2.

Hu, Wen-Xiang et al., "Synthesis of Mono-Ester of Alkylphosphonates," Acta Chemica Sinica, 1996, 54, pp. 77-83.

Gaboyard, M. et al., "Synthese et Etude Structurate D'Acides Alkylphosphoniques a Longue Chaine Hydrocarbonee," Phosphorus, Sulfur and Silicon, 2002, vol. 177, pp. 877-891.

Christol, Henri et al., "Hydrolyse Basique de Phosphonates I. Etude Qualitative," Journal of Organometallic Chemistry, 12, 1968, pp. 459-470.

Christol, Henri et al., "Hydrolyse Basique de Phosphonates II. Etude Quantitative," Journal of Organometallic Chemistry, 12, 1968, pp. 471-476.

Boutevin, B. et al., "Monodealkylation of Phosphonic Esters, Synthesis of Phosphonic Salts and Monoacids," Phosphorus, Sulfur and Silicon, 2001, vol. 174, pp. 1-14.

Saady, Mourad et al., "Selective Monodeprotection of Phosphate, Phosphite, Phosphonate and Phosphoramide Benzyl Esters," J. Org. Chem, 1995, 60, pp. 2946-2947.

Pienaar, Andre et al., "Synthesis of Alkyl Hydrogen Alkylphosphonates," Phosphorus, Sulfur and Silicon, 1999, vol. 148, pp. 149-159.

Hu, Wen Xiang et al., "Synthesis of Hindered Alkyl Phosphonates and Phosphonic and Phosphinic Acids," Chinese Chemical Letters, 1992, vol. 3, No. 3, pp. 167-170.

Pietzonka, et al., "Phosphonate-Containing Analogs of Cholesteryl Ester as Novel Inhibitors of Cholesteryl Ester Transfer Protein," Bioorganic & Medicinal Chemistry Letters, vol. 6, No. 16, 1996, pp. 1951-1954.

Chemical Abstracts; Yuan, Chengye et al: "Studies on organophosphorus compounds. XXIV. Synthesis of monobutyl esters of octylphosphonates;" XP002292189; retrieved from STN Database accession No. 1989:95370 "abstract" Huaxue Xuebao, 46(3), 290-3 CODEN: HHHPA4; ISSN: 0567-7351, 1988.

* cited by examiner

Primary Examiner—Kamal A. Saeed

(57) ABSTRACT

The present invention discloses a process for manufacturing an alkylphosphonate monoester. The process may comprise partially hydrolyzing an alkyl phosphonate diester with an alkaline compound in a first solvent to provide a reaction mixture, wherein the first solvent comprises a mixture of an alcohol and water. The reaction mixture may be diluted with a second solvent to provide an organic phase, wherein the second solvent comprises at least one non-polar organic solvent. The process may comprise acidifying the reaction mixture with an acid, wherein the organic phase includes an alkylphosphonate monoester.

3 Claims, 3 Drawing Sheets

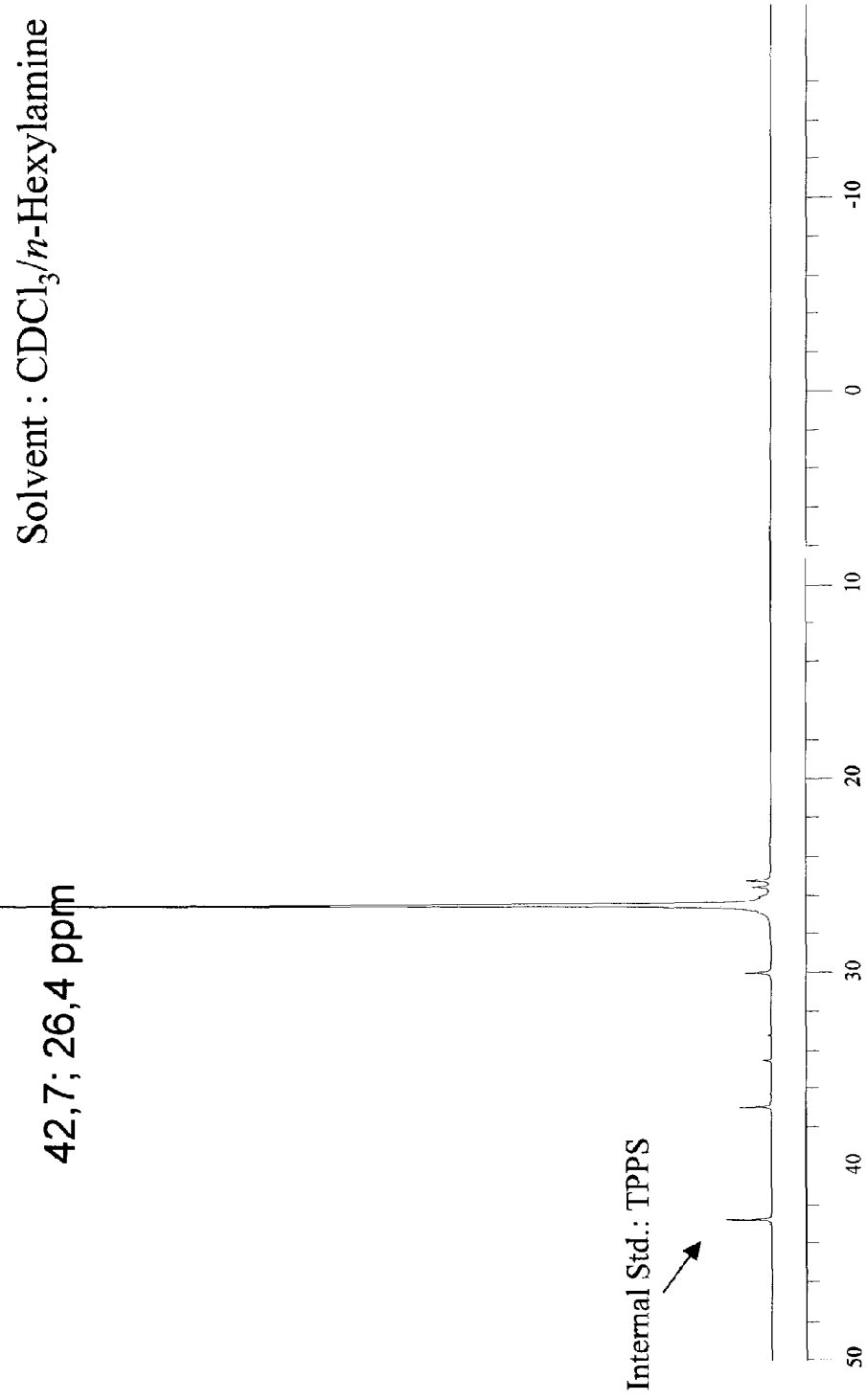
Figure 1. P³¹-NMR Spectrum of Octadecylphosphonic acid monomethyl ester

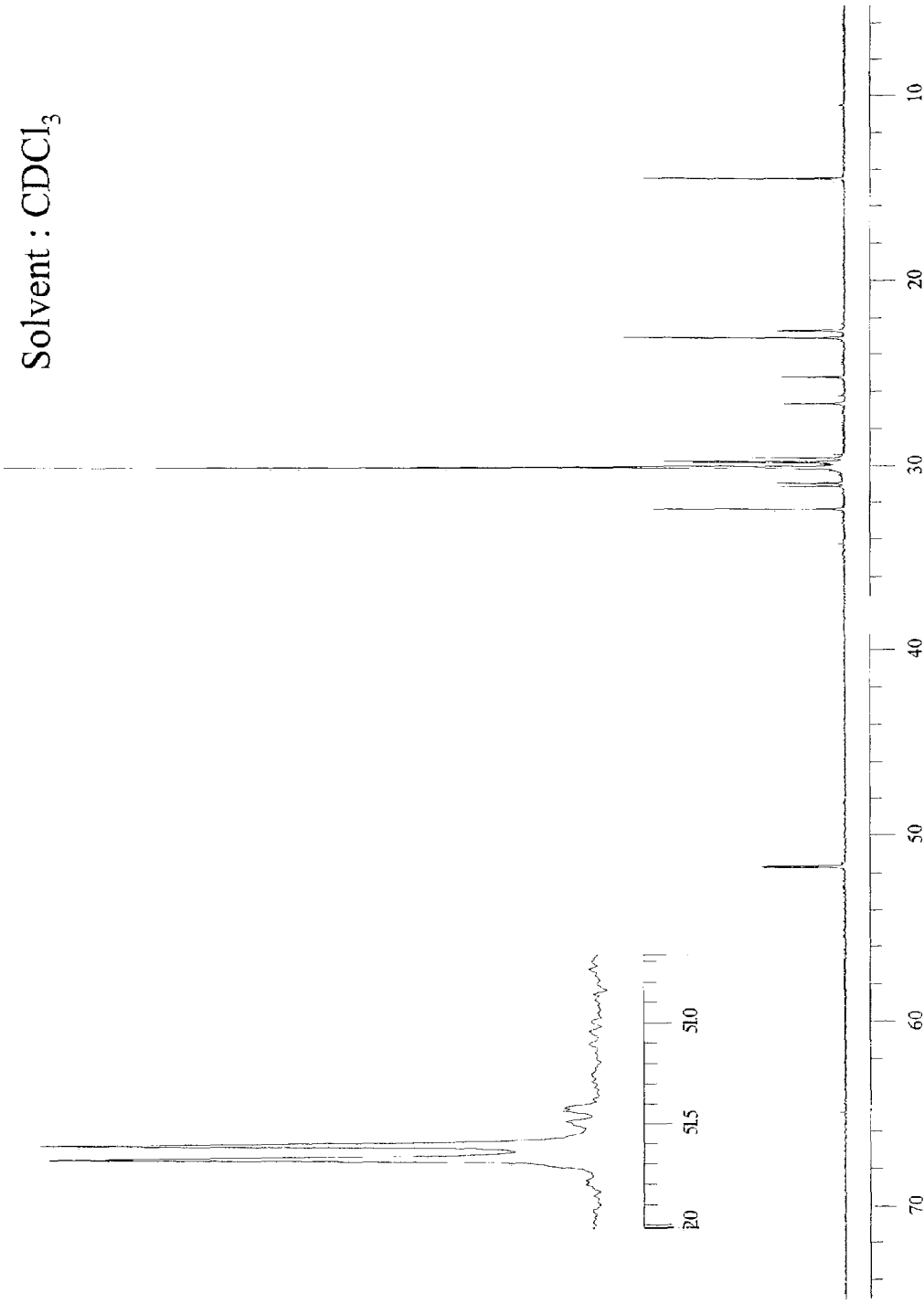
Figure 2. C[13]-NMR Spectrum of Octadecylphosphonic acid monomethyl ester

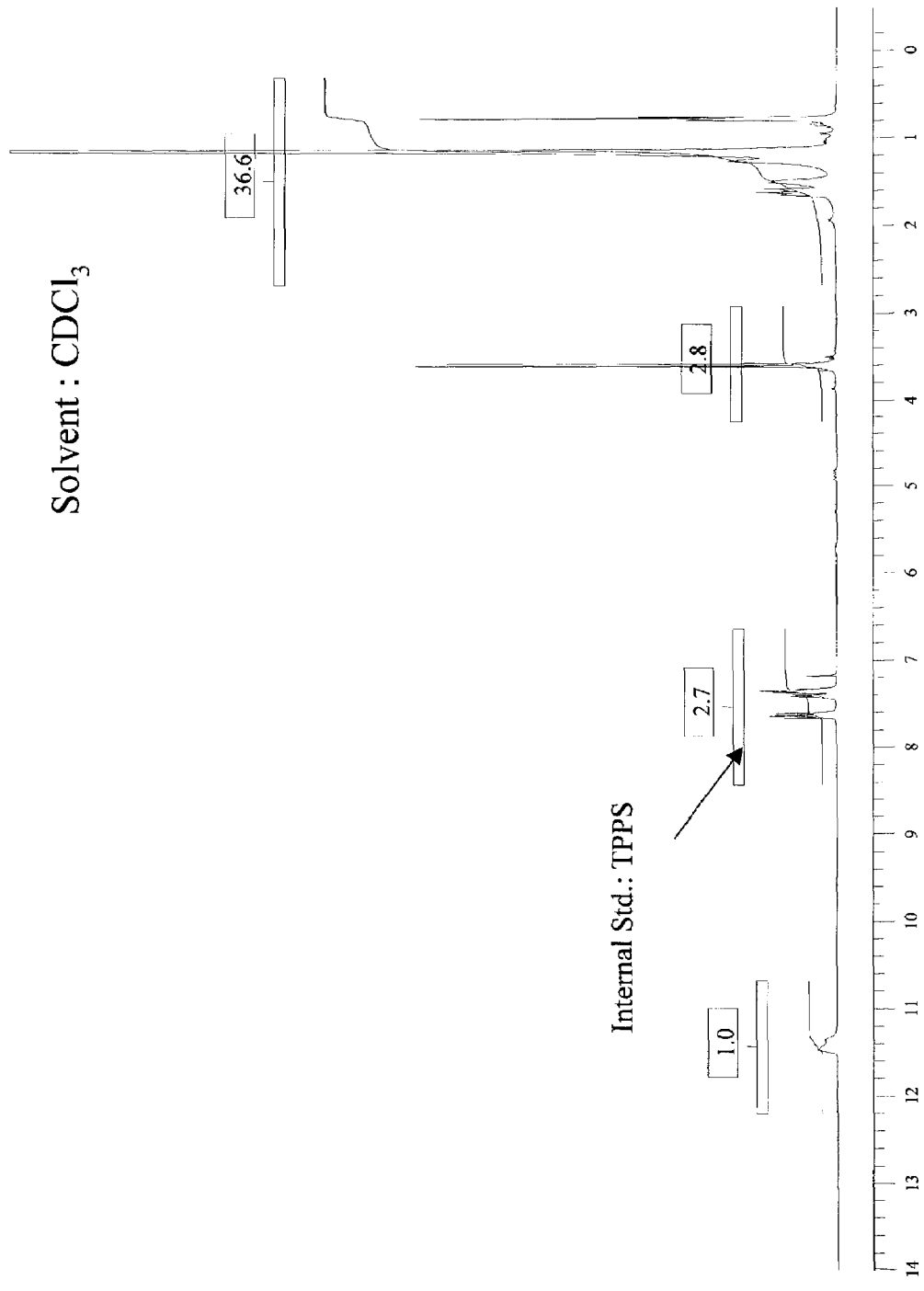
Figure 3. Proton NMR Spectrum of Octadecylphosphonic acid monomethyl ester
Solvent : CDCl$_3$
Internal Std.: TPPS

PROCESS FOR MANUFACTURING ALKYLPHOSPHONATE MONOESTERS

FIELD OF INVENTION

This invention relates to a process for manufacturing alkylphosphonate monoesters and compositions comprising alkylphosphonate monoesters manufactured according to such process. Alkylphosphonate monoesters are useful as additives for providing, for example, friction durability and/or anti-shudder performance, in lubricating fluids. More particularly, alkylphosphonate monoesters are useful as additives in power transmitting fluids, such as, automatic transmission fluids (ATF), manual transmission fluids, and/or continuously variable transmission (CVT) fluids.

BACKGROUND OF THE INVENTION

Current methods for the manufacture of alkylphosphonate monoester are accompanied by undesirable processing conditions, environmentally unfriendly components, and uneconomical by-products. For example, the hydrolysis of alkylphosphonate monoesters is most commonly carried out in an aqueous medium followed by neutralization with a mineral acid. This method however, causes gelation and foaming when applied to hydrophobic alkylphosphonate diesters. Other methods use low molecular weight ketones, such as acetone and methyl ethyl ketone, as solvents in the presence of sodium iodide (NaI). The resulting monoacid salts are converted to free acids with the use of ion exchange resins. Another approach is to use water-miscible solvents, like dioxane and THF, which raise health and environmental concerns. Further, many such methods require processing that involves handling of intermediates in a solid phase. Such handling is undesirable and, furthermore, decreases product yield and purity.

Therefore, a need exists in the art for an improved processing method that is economical, environmentally friendly, and provides an improved alkylphosphonate monoester.

BRIEF SUMMARY OF EMBODIMENTS

An embodiment of the present disclosure provides a process for manufacturing alkylphosphonate monoesters. Another embodiment of the present disclosure provides alkylphosphonate monoesters manufactured according to such a process. A further embodiment of the present disclosure provides a composition comprising alkylphosphonate monoesters manufactured according to such a process.

An embodiment of the present disclosure may relate to an economical and environmentally friendly process for preparation of alkylphosphonate monoesters which are widely used as lubricant additives. This process may comprise a mixed solvent system which can solubilize both metal hydroxides and water insoluble phosphonate esters to eliminate gelation and foaming problems. An embodiment may additionally or alternatively provide a process that avoids processing solid phase components. An embodiment may additionally or alternatively provide homogeneous liquid phase components, which provide improved processing conditions. An embodiment may additionally or alternatively provide an alkylphosphonate monoester that is oil soluble.

In an embodiment, a lubricant may comprise an alkylphosphonate monoester manufactured according to one or more methods herein described. Such a lubricant may improve performance in durability testing, such as friction durability testing.

An embodiment may comprise a process for manufacturing an alkylphosphonate monoester, comprising partially hydrolyzing an alkyl phosphonate diester with an alkaline compound in a first solvent to provide a reaction mixture, and wherein the first solvent comprises a mixture of an alcohol and water; diluting the reaction mixture with a second solvent to provide an organic phase, wherein the second solvent comprises at least one non-polar organic solvent; acidifying the reaction mixture with an acid, wherein the organic phase includes the alkylphosphonate monoester.

A embodiment may comprise a process for manufacturing an alkylphosphonate monoester, comprising reacting an alkyl phosphonate diester of formula (1) with suficient alkaline metal compound or alkaline earth metal compound and a solvent mixture comprising alcohol and water to provide salt of formula (2);

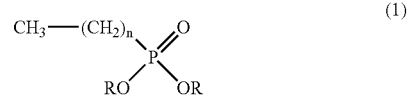

wherein, in formula (1), n is about 5 to about 25 including all possible linear, branched, or iso-alkyl isomers and wherein each R is independently selected from the group consisting of methyl, ethyl, propyl, isopropyl, n-butyl, t-butyl, isobutyl, or any combination thereof;

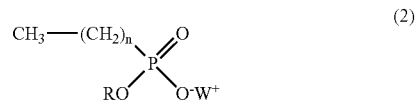

wherein, in formula (2), n is about 5 to about 25 including all possible linear, branched, or iso-alkyl isomers, wherein R is selected from the group consisting of methyl, ethyl, propyl, isopropyl, n-butyl, t-butyl, isobutyl, or any combination thereof, and wherein W is an alkaline metal or an alkaline earth metal;

adding sufficient acid to the reaction product of formula (2) to produce an alkylphosphonate monoester of formula (3),

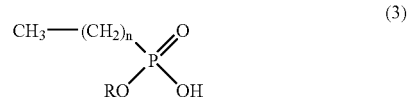

wherein n is about 5 to about 25 including all possible linear, branched, or iso-alkyl isomers and wherein R is selected from the group consisting of methyl, ethyl, propyl, isopropyl, n-butyl, t-butyl, isobutyl, or any combination thereof.

An embodiment may comprise an alkylphosphonate monoester manufactured according to a process of the present disclosure.

An embodiment may comprise a method of improving the friction durability of a power transmitting fluid comprising adding to a power transmitting fluid, an alkylphosphonate monoester manufactured according to a process of the present disclosure.

An embodiment may comprise a method of improving the anti-shudder durability of a power transmitting fluid comprising adding to a power transmitting fluid, an alkylphosphonate monoester manufactured according to a process of the present disclosure.

An embodiment may comprise an additive for a power transmitting fluid comprising an effective amount of an alkylphosphonate monoester manufactured according to a process of the present disclosure.

An embodiment may comprise a power transmitting fluid comprising a major amount of a base oil and an effective amount of an alkylphosphonate monoester manufactured according to a process of the present disclosure.

As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

BRIEF DESCRIPTION OF THE DRAWINGS

FIG. 1 shows $P^{31}$-NMR data based on spectroscopic data of an embodiment.

FIG. 2 shows $C^{13}$-NMR data based on spectroscopic data of an embodiment.

FIG. 3 shows H-NMR (or proton-NMR) data based on spectroscopic data of an embodiment.

DETAILED DESCRIPTION OF EMBODIMENTS

Alkylphosphonate monoesters are useful as additives for providing, for example, friction durability and/or anti-shudder performance, in lubricating fluids. More particularly, alkylphosphonate monoesters are useful as additives in a power transmitting fluid, such as, an automatic transmission fluid (ATF), a manual transmission fluid, and/or a continuously variable transmission (CVT) fluid (including a fluid designated an infinitely variable transmission (IVT) fluid). A lubricating fluid may comprise, for example, a power transmitting fluid, such as an automatic transmission fluid (ATF), a manual transmission fluid, a continuously variable transmission (CVT) fluid, or an infinitely variable transmission (IVT) fluid. A functional fluid may comprise a fully formulated fluid comprising a base oil, a lubricating fluid, and/or one or more additional additives.

An embodiment may comprise a process for manufacturing an alkylphosphonate monoester. The process may comprise the partial hydrolysis of a phosphonate diester with an alkaline compound in a solvent. Partial hydrolysis includes, for example, the hydrolysis of an ester group of the diester, whereas the other ester group of the diester is not hydrolyzed. The phosphonate diester may comprise a long carbon chain phosphonate diester. The phosphonate diester may comprise, for example, from about 6 carbon atoms to about 26 carbon atoms. As a further example, the phosphonate diester may comprise about 14 carbon atoms or more. As an even further example, the phosphonate diester may comprise about 18 carbon atoms. The phosphonate diester may comprise the structure of formula (1):

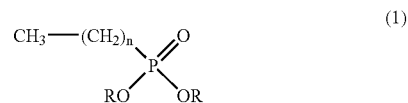

wherein n may be about 5 to about 25, including all possible linear, branched, or iso-alkyl isomers and wherein each R is independently selected from the group comprising methyl, ethyl, propyl, isopropyl, n-butyl, t-butyl, isobutyl, or any combination thereof.

In an embodiment of the present invention, the process may comprise alkaline hydrolysis of long-carbon-chain phosphonate diesters in water-alcohol mixed solvent system which may provide a homogeneous reaction medium for a fast and selective reaction.

The alkaline compound may comprise any of the Group I or Group II metals. In particular, the alkaline compound may comprise any alkaline metal and/or alkaline earth metal and/or a hydroxide thereof. For example, the alkaline compound may comprise potassium, calcium, magnesium, sodium, barium, or hydroxides thereof. The alkaline compound may comprise, for example, sodium hydroxide, potassium hydroxide, magnesium hydroxide, calcium hydroxide, barium hydroxide, aluminum hydroxide, and/or zinc hydroxide.

The solvent may comprise a solvent system or mixture. For example, the solvent may comprise a mixture of an alcohol and water. The alcohol may comprise a low molecular weight alcohol. The alcohol may comprise, for example, at least one of methanol, ethanol, propanol, isopropanol, n-butanol, t-butanol, pentanol, and iso and branched isomers thereof. Further, the alcohol may be miscible with water at reflux temperatures. The ratio of water to alcohol may be, for example, from about 1:10 to about 10:1 in weight percent of water to weight percent of alcohol in the solvent mixture. As a further example, the ratio of water to alcohol may be from about 1:4 to about 2:1 in weight percent of water to weight percent of alcohol in the solvent mixture. As an even further example, the ratio of water to alcohol may be about 1:1.1 in weight percent of water to weight percent of alcohol in the solvent mixture.

The molar ratio of an alkyl phosphonate diester to that of an alkaline metal compound may be about 1.0:1.5. The alkyl phosphonate diester of formula (1), for example, may react with sufficient alkaline metal or alkaline earth metal compound in the presence of the alcohol and water solvent mixture to provide a monoester salt of formula (2):

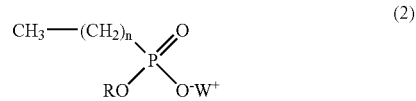

wherein n may be about 5 to about 25, including all possible linear, branched, or iso-alkyl isomers, wherein each R is selected from the group comprising methyl, ethyl, propyl, isopropyl, n-butyl, t-butyl, isobutyl, or any combination thereof, and wherein W is an alkaline metal or an alkaline earth metal.

The reaction mixture, for example the monoester salt of formula (2), may be diluted with a second solvent to provide an organic phase. The second solvent may comprise at least one non-polar organic solvent. The non-polar organic solvent may comprise, for example, one or more of a mineral oil, a synthetic oil, and/or a mixture thereof. As a further example, the non-polar organic solvent may comprise an alkane, a linear ether, a cyclic ether, a halogenated hydrocarbon, an aromatic hydrocarbon, a cycloalkane, and/or a mixture thereof. The non-polar organic solvent may be present in an amount from about 20 wt % to about 50 wt %.

The reaction mixture may be acidified with an acid. The acid may comprise a mineral acid, a carboxylic acid, a phosphoric acid, a phosphorous, acid, a hydrochloric acid, a nitric acid, a perchloric acid, a sulfuric acid, and/or a mixture or precursor thereof. Further, the acid may comprise any suitable base neutralizer. The acidified reaction mixture may form two liquid phases comprising an organic phase and a water phase. The two phases may then be separated to provide the organic phase. The phases may be separated from each other, for example, by gravity separation, by decanting, or by centrifugal force. The organic phase may be further processed, such as distilled, to provide the alkylphosphonate monoester. The alkylphosphonate monoester may be oil soluble and may comprise the structure of formula (3):

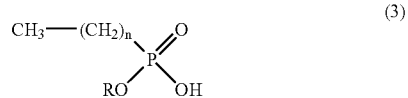

(3)

wherein n is about 5 to about 25, including all possible linear, branched, or iso-alkyl isomers and wherein R is selected from the group consisting of methyl, ethyl, propyl, isopropyl, n-butyl, t-butyl, isobutyl, or any combination thereof.

The alkylphosphonate monoester may comprise, for example, dialkyl alkylphosphonate and/or alkylphosphonic acid. The reaction product may be of high purity. For example, the organic phase may comprise from about 0.2 wt % or less to about 1.1 wt % or more of the diester. As a further example, the organic phase may comprise from about 0.6 wt % or less to about 1.1 wt % or more of the diester. As an even further example, the organic phase may comprise from about 0.75 wt % or less to about 1.1 wt % or more of the diester. Further, the organic phase may comprise about 95 wt % or more of alkylphosphonate monoester.

A chemical reaction that describes an embodiment of the present invention is shown below; where, n may comprise from about 5 to about 25 and include all possible linear, or n-, and branched or iso-alkyl isomers. For example, the alkyl groups may include 2-ethylhexyl, nonyl, decyl, isodecyl, dodecyl, hexadecyl, and octadecyl. R groups may be methyl, ethyl, propyl, isopropyl, butyl, isobutyl, or a combination thereof.

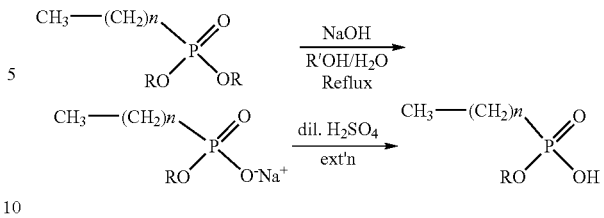

The manufacture of alkylphosphonate monoester according to the present invention includes many advantages, such as trouble free processing with a liquid phase during all stages of the reaction. The process according to the present invention does not require handling a solid phase or insolubility. Processing with a solid phase may pose certain disadvantages such as difficulty in handling and lower product yield. A further advantage includes the use of environmentally benign components and intermediates, thus posing low risk to those exposed to the reaction. Another advantage is that the reaction is highly selective, and very little diacid is produced. Thus, the present process minimizes waste of reactants in providing a high yield product. Another advantage is that the present process is fast compared to current processes, thus saving the manufacturer time, and allowing higher volume production in shorter times.

A lubricating fluid, for example for use in a power transmitting fluid, may derive benefits and advantages by including alkylphosphonate monoester manufactured according to a process of the present invention. In particular, the fluid may have improved durability and/or may have improved anti-shudder performance. A further advantage is that the initial friction (the ability to transmit power to the tires) is lowered, and thus improved. Further, initial torque performance may also be improved by incorporating alkylphosphonate monoester manufactured according to a process of the present invention.

An alkylphosphonate monoester compound manufactured according to an embodiment of the present invention will be about twice as effective in the Low Velocity Friction Apparatus ("LVFA") Durability test at extending duration of the friction durability of a power transmitting fluid including the monoester compound compared to a power transmitting fluid containing a diester counterpart. Therefore, use of such a monoester compound will allow the formulator to use about 50% less of such component to achieve results comparable to those achieved by use of a diester (or unhydrolyzed) counterpart component.

For example, power transmitting fluid test samples were tested using a Low Velocity Friction Apparatus ("LVFA") Durability test system (JASO M349). The test samples included a monoester compound, a diester compound, or neither. Durability was demonstrated in number of hours until the friction coefficient versus velocity comparison showed a negative slope. This data was then analyzed using linear regression analysis. The regression coefficient evidenced that the fluid containing the monoester compound was about twice as effective in extending the durability of the fluid compared to the fluid containing the diester.

A lubricating fluid according to the present invention may include other advantageous additives to improve the characteristics of that fluid, and which ultimately relate to improvement of the overall vehicle performance and fuel economy. Such additives may comprise, for example, one or more of any or none of an extreme pressure agent, an antiwear agent, an antioxidant or an antioxidant system, a corrosion inhibitor or a corrosion inhibitor system, a metal deactivator, an anti-rust agent, a friction modifier, a dispersant, a detergent, a dye, a seal swell agent, an anti-foam agent, a surfactant, a viscosity index improver, a viscosity modifier, a perfume or odor mask, and any suitable combinations thereof. For example, while friction modifiers may be routinely added to lubricating fluids, the particular type and amount of friction modifier is unique and specific to the needs of each particular application.

Further, a lubricating fluid according to the present invention may be used in combination with a base oil. The base oil may comprise any suitable base oil or mixture of base oils for a particular application. In some embodiments of the present invention, additives may be provided in an additive package concentrate. The alkylphosphonate monoester may comprise an additive in an additive package. In particular, an additive package for a power transmitting fluid, such as an ATF, a MTF, or a CVT fluid may comprise an effective amount of an alkylphosphonate monoester made according to the present invention. An effective amount may comprise an amount suitable to provide enhanced anti-shudder properties and/or improved friction durability.

Further, some embodiments of the present invention may comprise a diluent, e.g., a diluent oil. A diluent may be included to ease blending, solubilizing, and transporting the additive package. The diluent may be compatible with a base oil and/or the additive package. The diluent may be present in any suitable amount in the concentrate. A suitable diluent may comprise a process oil of lubricating viscosity. Suitable base stocks may be manufactured from the gas-to-liquid process.

EXAMPLE 307 g of dimethyl octadecylphosphonate (DMOP), 172 g $H_2O$, and 184 g n-propyl alcohol were charged into a 2 liter round bottomed flask equipped with a condensor, thermocouple probe, and a mechanical stirrer. To this stirred solution was added 44.0 g sodium hydroxide (NaOH) in one portion at 70° C. After the initial exotherm subsided, the stirred mixture was heated to maintain a fast reflux (87° C.) for 3 hours. The clear deep yellow solution was cooled to 65° C. and diluted with 260 mL of heptane. The stirred solution containing phosphonic acid sodium salt was acidified (pH=3–3.5) with 20% $H_2SO_4$. After 5 min of vigorous stirring the mixture was allowed to separate into liquid layers. The dense aqueous layer was drawn through a stopcock at the bottom of the reaction flask. The organic layer in the flask was separated from the solvent by vacuum distillation (25–28 mm Hg) to leave a dense liquid residue at 125° C. The dense liquid residue was poured out of the flask. The product weighed 293.2 g (99.3% recovery). It gave the analytical and spectroscopic data shown in FIGS. 1–3.

An Inductively Coupled Plasma ("ICP") analysis showed favorable agreement between calculated phosphorus content and percentage determined by ICP. The percent phosphorus was about 9.00%, whereas the calculated phosphorus content was about 8.89%. The total acid number ("TAN") value was determined using ASTM D664 and was about 165.8 mg KOH/g (calculated value was about 160.9 mg KOH/g). This value supports the resulting high level of product purity. A quantitative determination of impurities was carried out by $P^{31}$-NMR that involved spiking experiments using authentic samples.

In FIG. 1, $P^{31}$-NMR spectrum of octadecylphosphonic acid monomethyl ester illustrates peaks of the component in a $CDCl_3$ and n-hexylamine solvent system. In FIG. 2, $C^{13}$-NMR spectrum of octadecylphosphonic acid monomethyl ester illustrates peaks of the component in $CDCl_3$. In FIG. 3, H-NMR (or proton NMR) spectrum of octadecylphosphonic acid monomethyl ester illustrates peaks of the component in $CDCl_3$. These figures show that the amount of impurity in the product may be up to about 10%. In particular, the product may contain about 0.25% dimethyl octadecyl phosphonate diester (DMOP) and/or about 0.6% fully hydrolyzed dimethyl phosphonate diester.

While the present disclosure has been described in some detail by way of illustration and example, it should be understood that the embodiments are susceptible to various modifications and alternative forms, and are not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A lubricant comprising an alkyphosphonate monoester manufactured by:
   partially hydrolyzing an alkylphosphonate diester with an alkaline compound in a first solvent to provide a reaction mixture, wherein the first solvent comprises a mixture of an alcohol and water;
   diluting the reaction mixture with a second solvent to provide an organic phase, wherein the second solvent comprises at least one non-polar organic solvent;
   acidifying the reaction mixture with an acid, wherein the organic phase includes an alkylphosphonate monoester.

2. An additive for a power transmission fluid, comprising:
   an effective amount of an alkylphosphonate monoester manufactured by a process comprising:
   partially hydrolyzing an alkyl phosphonate diester with an alkaline compound in a first solvent to provide a reaction mixture, and wherein the first solvent comprises a mixture of an alcohol and water;
   diluting the reaction mixture with a second solvent to provide an organic phase, wherein the second solvent comprises at least one non-polar organic solvent;
   acidifying the reaction mixture with an acid, wherein the organic phase includes an alkylphosphonate monoester.

3. A power transmitting fluid comprising a major amount of a base oil and an effective amount of an alkylphosphonate monoester manufactured by a process comprising:
   partially hydrolyzing an alkyl phosphonate diester with an alkaline compound in a first solvent to provide a reaction mixture, and wherein the first solvent comprises a mixture of an alcohol and water;
   diluting the reaction mixture with a second solvent to provide an organic phase, wherein the second solvent comprises at least one non-polar organic solvent;
   acidifying the reaction mixture with an acid, wherein the organic phase includes an alkylphosphonate monoester.

* * * * *